United States Patent [19]
Falb et al.

[11] Patent Number: 5,253,640
[45] Date of Patent: Oct. 19, 1993

[54] PROCESS FOR THE CALIBRATION OF A FLOW SENSOR IN A RESPIRATORY SYSTEM

[75] Inventors: Wolfgang Falb, Krummesse; Karl-Ludwig Gippert; Ulrich Heim, both of Lübeck; Uvo Hölscher, Stockelsdorf; Siegfried Kiske, Gross Grönau; Götz Kullik, Lübeck; Ralf-Ernst Löser, Kreuzkamp; Christoph Mauer, Bad Schwartau, all of Fed. Rep. of Germany

[73] Assignee: Drägerwerk Aktiengesellschaft, Lübeck, Fed. Rep. of Germany

[21] Appl. No.: 833,309

[22] Filed: Feb. 10, 1992

[30] Foreign Application Priority Data

Apr. 12, 1991 [DE] Fed. Rep. of Germany ....... 4111965

[51] Int. Cl.⁵ ........................................... A61M 16/01
[52] U.S. Cl. ........................ 128/200.24; 128/203.12; 128/205.18
[58] Field of Search ..................... 128/200.24, 203.12, 128/203.14, 204.21, 205.18, 205.19, 205.13

[56] References Cited

U.S. PATENT DOCUMENTS

| | | | |
|---|---|---|---|
| 4,587,967 | 5/1986 | Chu | 128/204.21 |
| 4,637,386 | 1/1987 | Baum | 128/204.21 |
| 4,957,107 | 9/1990 | Sipin | 128/204.21 |
| 5,165,397 | 11/1992 | Arp | 128/204.21 |

Primary Examiner—Edgar S. Burr
Assistant Examiner—Eric P. Raciti
Attorney, Agent, or Firm—McGlew and Tuttle

[57] ABSTRACT

A process for calibrating a flow sensor in a respiratory system, with final control elements arranged in the respiratory system for influencing the respiration gas stream, is to be improved in terms of the influence of the qualitative gas composition of the respiration gas. To accomplish the task, the final control elements 4, 11 are switched, for calibration, over to a closed respiratory system with directed respiration gas stream. The drive unit 13 feeds the respiration gas present in the respiratory system through the flow sensor 9 according to a predetermined time-volume relationship. A calibration value for the flow sensor 9 is formed by comparison of the time-volume relationship with the measured signal of the flow sensor 9.

20 Claims, 1 Drawing Sheet

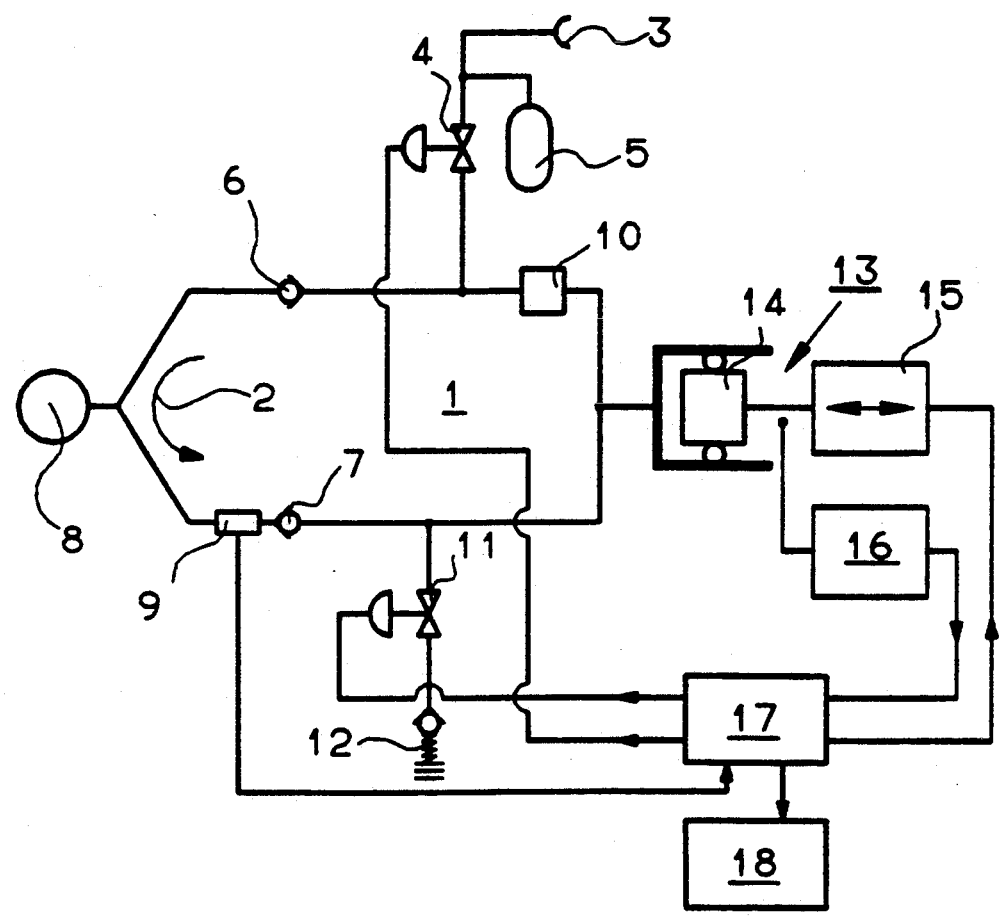

PROCESS FOR THE CALIBRATION OF A FLOW SENSOR IN A RESPIRATORY SYSTEM

FIELD OF THE INVENTION

The present invention pertains to a process for calibrating a flow sensor in a respiratory system, and more particularly to a respiratory system wherein control elements are provided for influencing the respiration gas stream in a drive unit for feeding the respiration gas stream.

BACKGROUND OF THE INVENTION

A respiratory system with a flow sensor has become known from DE-A1-34,34,908. The respiratory system contains nonreturn valves as final control elements and direction valves which control the flow of the respiration gas stream. Fresh gas is fed into the respiratory system via a fresh gas connection and a first nonreturn valve. On the inspiration side, the respiration gas flows through a carbon dioxide absorber, a first directional valve and a pressure sensor and to the lung of a patient; on the expiration side, there are a flow sensor and a second directional valve, via which the respiration gas is returned into the inspiration arm. A second nonreturn valve for releasing excess respiration gas and a drive unit with variable volume are provided in the respiratory system, and the drive unit feeds respiration gas to the patient's lung in a rhythmic sequence. The course of respiration over time is determined by a control unit.

Different forms of respiration can be realized by correspondingly actuating the nonreturn valves. A so-called closed respiratory system is obtained when only as much fresh gas is metered into the respiratory system as is consumed by the patient, while in a semi-closed respiratory system, one operates with excess fresh gas and the excess respiration gas is released from the respiratory system after each breath.

Respiration is monitored with a pressure sensor for the respiration pressure and a flow sensor which measures the volume expired by the patient. One widely used embodiment of a flow sensor is based on constant-temperature hot wire anemometry. This measurement method depends on the type of the gas, on the one hand, and, on the other hand, a reference value for "zero" flow must be available in the measuring device. Concerning correction for the effect of the type of the gas, compensation methods are known which are able to take binary gas mixtures containing known components, e.g., laughing gas and oxygen, adequately into account. However, these compensation methods are unable to evaluate gas mixtures containing more than two components. Three components are present, e.g., when anesthetic is also metered into the respiratory system in addition to oxygen and laughing gas. The influence of the anesthetic on flow measurement is negligible if anesthetics to be metered at low doses are used, at concentrations of up to ca. 4%.

In contrast, the accuracy of measurement of the flow sensor can be expected to be reduced in the case of anesthetics to be metered at high doses (up to 20%).

The reference value for "zero" flow is usually obtained by turning off the drive unit and measuring the reference value with the respiration gas stream stopped. However, it is also possible to determine this reference value during the reversal pause between inspiration and expiration.

SUMMARY AND OBJECTS OF THE INVENTION

It is a primary object of the present invention to improve the method for calibrating a flow sensor in a respiratory system.

The task is accomplished in that the final control element is switched over to a closed respiratory system with directed respiration gas stream for the calibration, the drive unit feeds the respiration gas present in the respiratory system via the flow sensor according to a predetermined time-volume relationship, and a calibration value is formed for the flow sensor by comparing the time-volume relationship with the measured signal of the flow sensor.

The advantage of the present invention is essentially the fact that the respiration gas is fed from the closed respiratory system with the drive unit via the flow sensor according to a predetermined time-volume relationship, and the calibration value for the flow sensor is formed by comparing the volume fed per unit time with the measured signal of the flow sensor. Thus, to calibrate the flow sensor, the respiration gas is used in the composition in which it happens to be present in the respiratory system. Because of the closed respiratory system, no fresh gas is able to flow into the respiratory system and no respiration gas is able to escape. The time-volume relationship is established in the control unit and is sent to the drive unit. Thus, the respiration gas volume per unit time which flows through the flow sensor is known. The reference value for the "zero" flow state is determined in the known manner, e.g., by measuring the reference value with the flow sensor in stagnant respiration gas flow prior to turning on the drive unit.

It is advantageous to use a piston-cylinder assembly unit with a drive, which has a displacement-measuring device for the piston stroke, as the drive unit. An accurate displacement-volume relationship can be realized with this embodiment. The time can be taken into account by withdrawing the piston at a defined velocity, preferably a constant velocity. With the known displacement-volume relationship and known time (piston withdrawn at constant velocity over displacement range), the aforesaid time-volume relationship is established. The respiration gas stream is routed through the directional valves in the respiratory system so that the respiration gas is fed through the flow sensor during the expiration phase.

It is advantageous to perform the calibration of the flow sensor periodically. Continuous adjustment of flow measurement to the qualitative composition of the respiration gas is thus possible. However, it is also possible to initiate a calibration cycle by the control unit at the time of transition from the induction phase to the maintenance phase of anesthesia.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic representation of the respiratory system of the invention.

DETAILED DESCRIPTION OF THE PREFERRED EMBODIMENT

The only FIGURE shows a respiratory system 1, in which the respiration gas circulates in the direction of the direction arrow 2. At a fresh gas connection 3, fresh gas is fed into the respiratory system 1 via a first final control element 4, which is preceded by a breathing bag 5 serving as a buffer volume. A first directional valve 6 and a second directional valve 7 determine the direction of flow of the respiration gas to the patient 8 and back via a flow sensor 9, which determines the amount of respiration gas expired. The carbon dioxide expired by the patient 8 is removed from the respiration gas with a carbon dioxide absorber 10. A second final control element 11, with which excess respiration gas can be released from the respiratory circulation 1 via a nonreturn valve 12, is located behind the second directional valve 7 in the direction of flow.

The respiration gas is delivered with a drive unit 13, which consists of a piston-cylinder unit 14 and a drive 15.

The displacement of the piston of the piston-cylinder unit 14 is measured with a displacement-measuring device 16. The final control elements 4, 11 and the drive 15 are controlled via a control unit 17, which receives the current displacement value of the piston-cylinder unit 14 via the displacement-measuring device 16. The flow sensor 9 is also connected to the control unit 17, and the measured flow values are displayed on a display unit 18.

The calibration of the flow sensor 9 is performed as follows:

At the end of the inspiration stroke, the piston of the piston-cylinder unit 14 is located at its left-hand stop, i.e., the respiration gas is fed completely into the respiratory system 1. The final control elements 4, 11 are subsequently closed, so that no fresh gas is able to flow into the respiratory system 1, and no respiration gas escapes via the nonreturn valve 12. The "zero" flow value is first measured as a reference value with stagnant respiration gas flow. The piston of the piston-cylinder unit 14 is then withdrawn at constant velocity according to a displacement-volume relationship preset by the control unit 17, and the respiration gas is delivered via the flow sensor 9. The calibration value for the flow sensor 9 is formed by comparison of the measured value sent by the flow sensor 9 to the control unit 17 with the displacement-volume relationship. The time can be taken into account by withdrawing the piston at a defined velocity, preferably a constant velocity, to provide a time volume relationship.

To adjust the calibration to a qualitatively different gas composition, it is necessary to periodically repeat the calibration.

While a specific embodiment of the invention has been shown and described in detail to illustrate the application of the principles of the invention, it will be understood that the invention may be embodied otherwise without departing from such principles.

What is claimed is:

1. A process for calibrating a flow sensor in a respiratory system with final control elements arranged in the respiratory system for feeding gas to and withdrawing gas from a respiration gas stream, in communication with lungs of a patient and with a drive unit for imparting flow to the respiration gas stream, the process for calibrating comprising the steps of:

actuating each of said final control elements to switch said respiratory system to a closed respiratory system, wherein gas is neither fed nor withdrawn from said respiration gas stream, with directed respiration gas flow between lungs of the patient and said closed respiratory system;

activating the drive unit to feed the respiration gas present in the closed respiratory system through the flow sensor according to a predetermined time-volume relationship; and forming a calibration value for the flow sensor by comparison of the time-volume relationship with a measured signal of the flow sensor.

2. A process according to claim 1, further comprising: providing said drive unit in the form of a piston-cylinder unit with a drive and providing a displacement-measuring device, and measuring a piston stroke with said displacement-measuring device.

3. A process according to claim 1, further comprising forming said calibration value periodically.

4. A process according to claim 2, further comprising forming said calibration value periodically.

5. A process according to claim 1 wherein said step of forming a calibration value includes forming a reference value during a no flow condition sensed by said flow sensor, said no flow condition occurring either prior to activating said drive unit or during a reversal pause between inspiration and expiration.

6. An apparatus for calibrating a flow sensor in a respiratory system, comprising:

a respiratory circuit with a respiration gas stream in communication with lungs of a patient and including a first and second connection;

a first control element connected to said first connection for opening and closing said first connection;

a second control element connected to said second connection for opening and closing said second connection, said respiratory circuit with said first connection closed and said second connection closed forming a closed respiratory system wherein said respiration gas stream is maintained in said respiratory circuit and in communication with lungs of the patient;

drive means for feeding respiration gas present in said closed respiratory system through said flow sensor according to a predetermined time-volume relationship; and means for forming a calibration value by comparison of said time-volume relationship with a measured signal of said flow sensor.

7. An apparatus for calibrating a flow sensor in a respiratory system according to claim 6, wherein said drive means includes a piston-cylinder unit with a drive element and a displacement-measuring device for measuring displacement of a piston stroke.

8. An apparatus according to claim 6, wherein said means for forming a calibration value forms a reference value during a no flow condition sensed by said flow sensor, said no flow condition occurring either prior to said drive means feeding respiration gas or during a reversal pause between inspiration and expiration.

9. An apparatus according to claim 6, wherein a fresh gas connection and a breathing bag are connected to said first connection via a first connection line with said first control element positioned in said first connection line.

10. An apparatus according to claim 9, wherein a nonreturn valve is connected to said second connection to provide an excess respiration gas release for exhausting excess respiration gas from said respiratory circuit, said second control element being positioned between said second connection and said nonreturn valve.

11. An apparatus according to claim 10, wherein said drive means includes a constant velocity drive, and a displacement measuring device for measuring a piston stroke to formulate said predetermined time-volume relationship based on a piston stroke at said constant velocity.

12. A process for calibrating a flow sensor in a respiratory system including a respiratory circuit with a first and second connection and a patient respiration connection in communication with lungs of a patient, a first control element for opening and closing said first connection, a second control element for opening and closing said second connection, directional control means in said respiratory circuit for maintaining flow in one direction only, and a drive unit for circulating respiration gas within said circuit, the process for calibrating comprising the steps of:

acting on said first control element and said second control element to close said first connection and said second connection to confine the respiration gas stream to said respiratory circuit including said patient respiration connection in communication with lungs of the patient;

activating said drive unit and feeding respiration gas from said patient respiration connection of said respiratory circuit through said flow sensor at a predetermined volume rate of flow; and forming a calibration value by assigning said predetermined volume rate of flow to a signal measured by said flow sensor during said step of feeding respiration gas.

13. A process according to claim 12, further comprising: providing said drive unit as a piston cylinder unit, and providing a displacement-measuring device for measuring a piston stroke, said predetermined volume rate of flow being established based on said piston moving at a constant velocity over a measured piston stroke distance.

14. A process according to claim 12, wherein said step of forming a calibration value includes forming a reference value during a no flow condition sensed by said flow sensor, said no flow condition occurring prior to activating said drive unit or during a reversal pause between inspiration and expiration.

15. A process according to claim 12, wherein said respiratory circuit includes an inspiration branch, with flow directed from the said drive unit to said respiratory circuit and an exhalation branch with flow directed from said patient respiration connection to said drive unit, said flow sensor being positioned in said expiration branch.

16. An apparatus for calibrating a flow sensor in a respiratory system, comprising:

a respiratory circuit including a first connection, a second connection, and a respiration connection;

a first control element connected to said first connection for opening and closing said first connection;

a second control element connected to said second connection for opening and closing said second connection;

flow regulation means for restricting flow through said respiratory circuit to a single direction;

a flow sensor connected in said respiratory circuit for measuring flow of respiratory gas therethrough;

control means for acting on said first control element for closing said first control element and acting on said second control element for closing said second control element to define a closed respiratory system wherein respiratory gas in said respiratory circuit is confined to said respiratory circuit;

drive means for feeding respiration gas present in said closed respiratory system from said respiration connection through said flow sensor at a predetermined volume rate of flow.

17. An apparatus according to claim 16, further comprising calibration means connected to said flow sensor for forming a calibration value by assigning said predetermined volume rate of flow as an output corresponding to a measured signal of said flow sensor.

18. An apparatus according to claim 17, wherein said drive means comprises a piston-cylinder unit connected to a displacement measuring device for measuring a piston stroke, and a drive element for driving said piston at a constant velocity, said piston stroke and said constant velocity determining said volume rate of flow.

19. An apparatus according to claim 16, wherein said control means forms a reference value during a no flow condition sensed by said flow sensor, said no flow condition occurring either prior to, said drive means feeding respiration gas or during a reversal pause between inspiration and expiration.

20. An apparatus according to claim 16, wherein said respiratory circuit includes an inspiration line, with fluid flow from said drive means to said respiration connection, and an expiration branch with fluid flow from said respiration connection to said drive means, a fresh gas connection and a breathing bag being connected to said first connection via said first control element, a non-return valve for exhausting excess respiration gas being connected to said second connection via said second control element, said flow sensor being connected in said expiration branch.

* * * * *